United States Patent [19]

Schainholz

[11] Patent Number: 4,661,326
[45] Date of Patent: Apr. 28, 1987

[54] STERILIZATION CONTAINER

[76] Inventor: Herbert Schainholz, 316 Locust St., Teaneck, N.J. 07006

[21] Appl. No.: 704,873

[22] Filed: Feb. 25, 1985

[51] Int. Cl.[4] .......................... A61L 2/10; B65D 81/21
[52] U.S. Cl. ..................................... 422/310; 206/439; 220/371; 220/373; 422/297; 422/300
[58] Field of Search .................. 422/26, 34, 297, 300, 422/310; 220/371–374, 325, 327; 206/571, 363, 364–366, 438, 439; 55/325, 332, 444–446; 215/227, 261

[56] References Cited

U.S. PATENT DOCUMENTS

| | | | |
|---|---|---|---|
| 1,125,966 | 1/1915 | Combemale | 55/446 |
| 1,807,983 | 6/1931 | Hegan et al. | 55/325 |
| 1,857,348 | 5/1932 | Bokenkroger | 55/446 |
| 3,072,284 | 1/1963 | Luhman | 220/374 |
| 3,283,939 | 11/1966 | Miller | 220/374 X |
| 3,741,427 | 6/1973 | Doyle | 220/374 X |
| 3,858,752 | 1/1975 | Marvin et al. | 220/325 |
| 3,951,300 | 4/1976 | Kalasek | 220/327 |
| 4,213,537 | 7/1980 | Caccavale | 220/374 X |
| 4,296,862 | 10/1981 | Armentrout et al. | 220/374 X |
| 4,416,417 | 11/1983 | Sanderson et al. | 236/92 R |
| 4,512,498 | 4/1985 | Leibinger | 220/371 |

FOREIGN PATENT DOCUMENTS

| | | | |
|---|---|---|---|
| 2839219 | 3/1980 | Fed. Rep. of Germany . | |
| 438567 | 5/1912 | France | 422/300 |
| 2375869 | 7/1978 | France | 422/300 |
| 2542200 | 9/1984 | France | 422/297 |
| 22810 | 10/1901 | Switzerland . | |
| 164675 | 12/1933 | Switzerland . | |
| 21464 | of 1910 | United Kingdom | 422/300 |

OTHER PUBLICATIONS

"Eagle Steriset Technical Report", Kagan, AMSCO, Nov., 1983.

Primary Examiner—Barry S. Richman
Assistant Examiner—William R. Johnson
Attorney, Agent, or Firm—McAulay, Fields, Fisher, Goldstein & Nissen

[57] ABSTRACT

Openings are provided in the walls of a sterilization container, particularly one for surgical instruments, to allow for the introduction of a sterilant gas, and a filter element is provided internally of these openings. To prevent external objects from entering the openings in the surface and penetrating the filter element, a relatively stiff perforate sheet, preferably formed of metal, is placed between the surface of the container and the filter element, the perforations in the sheet being offset from the openings in the container wall.

6 Claims, 5 Drawing Figures

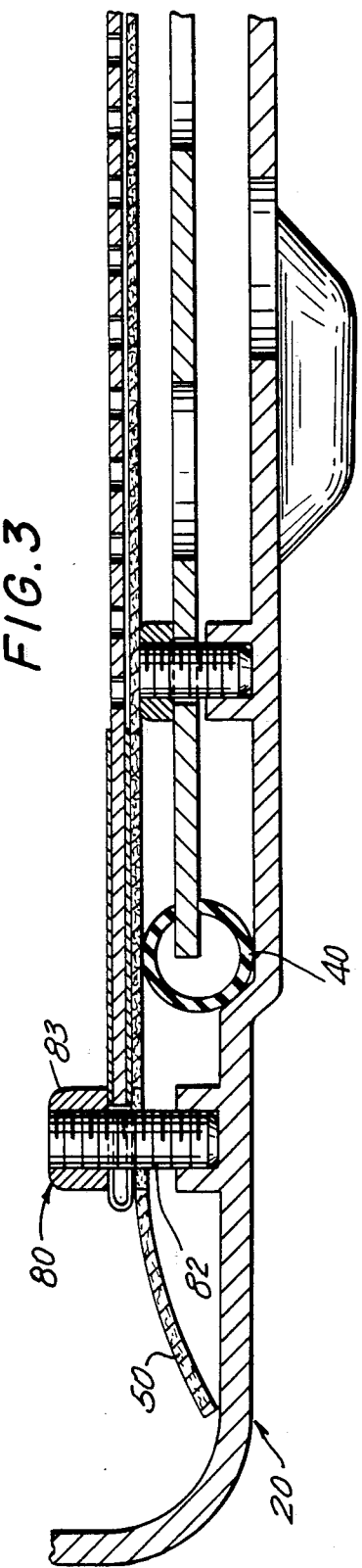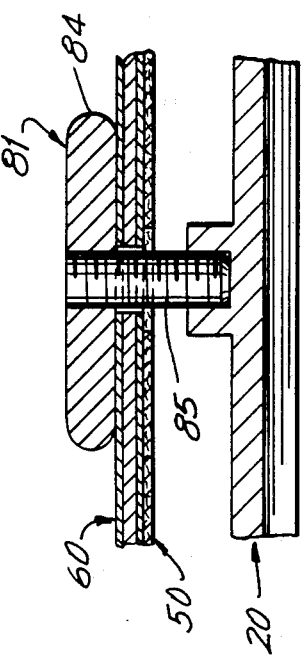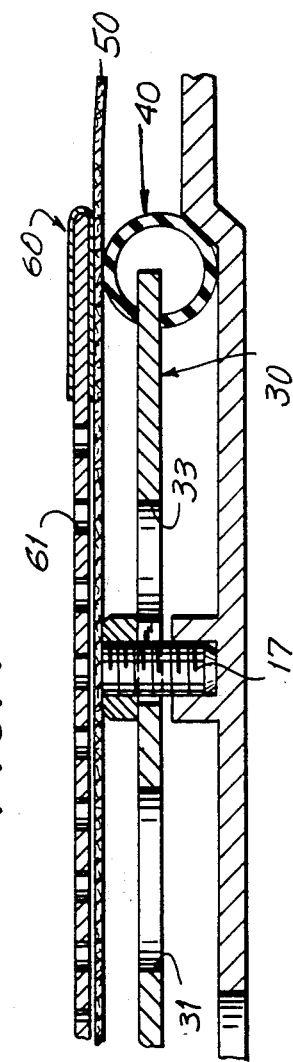

4,661,326

STERILIZATION CONTAINER

BACKGROUND OF THE INVENTION

The present invention is directed to a sterilization container within which sterilization trays are supported to sterilize surgical instruments. More particularly, the present invention is directed to a means for assuring the integrity of sterilization of the contents of the container during storage. A description of the use of sterilization trays, of the type held within the sterilization container of the present invention is described, for example, in my prior U.S. Pat. No. 4,135,868, issued Jan. 23, 1979.

Surgical instruments are frequently sterilized in sets so that all of the instruments required for a particular type of surgery, e.g., eye surgery, joint surgery, etc., are sterilized together and then taken, as a set, to the operating room where they are to be used.

In accomplishing the sterilization, the instruments to be sterilized are placed in baskets or holders of some type, and these baskets or holders are then placed within a container. The particular configuration of the baskets or holders form no part of the present invention.

The containers into which the instruments to be sterilized have been, placed, and the particular baskets or holders, are then transported to a chamber where sterilization is carried out. Frequently, sterilization involves treatment with high temperature steam or with ethylene oxide gas. In order to allow the steam or ethylene oxide gas to penetrate into the container and sterilize the instruments which are held within it, openings are provided in the walls of the container and, generally, a bacterial filter is placed adjacent these openings to assure the integrity of the items held within the container.

Unfortunately, the very openings which are required in the sides of the container to allow for entry of the sterilant provide the means for accidental or intentional loss of sterilization, as by puncturing of the bacterial filter with a sharp, or relatively sharp, instrument. For example, passage of a hypodermic needle through the openings and the filter allow for ingress of contaminating elements such that the sterility of the contents is destroyed; as is well known, this can lead to infection during the surgical procedure.

It is an object of this invention to provide, simply, for protection of a sterilization container against accidental or intentional loss of sterility within a sterilization container while still providing the ability to sterilize the contents of such a container.

SUMMARY OF THE INVENTION

In accordance with the present invention, a sterilization container is provided having surface openings which allow for the ingress of a sterilizing material, such as high temperature steam or ethylene oxide gas. Generally, the opening involves a series of perforations in the surface, each perforation being about ¼ to ½ inch in diameter, and the total of the perforations providing an open space of approximately 20% of the surface. It is through these openings, absent the structure of the present invention, through which accidental or intentional damage can be caused.

Immediately inside the container, and adjacent the openings in the surface, in accordance with the present invention, a perforated sheet is placed. This perforated sheet has openings which essentially duplicate the openings in the surface in both size and total area. Mounting means are provided on the inside of the container for holding this sheet in place in such a manner that the individual openings are offset from each other preventing a sharp object from penetrating both the openings in the surface and the openings in the additional perforated sheet. A gasket is placed between the perforated sheet and the surface both to maintain the perforated sheet in position and to aid in retention of sterility in the container.

On the side of the perforated sheet opposite the surface of the container, a bacterial filter, of any desired constituency, is placed and this is held firmly against the perforated sheet by another retaining member, this retaining member being provided with a plurality of small openings, the total area of the openings being essentially the same total area as the perforations in the surface of the container and the additional sheet.

With the structure just described, sterilant materials, such as high temperature steam and ethylene oxide gas may freely enter the sterilization container, but the bacterial filter and contents of the container are protected from loss of sterility due to the intrusion of foreign objects from outside the container.

DESCRIPTION OF THE DRAWINGS

In the accompanying drawings:

FIG. 3 is a sectional view along the line 3—3 of FIG. 2;

FIG. 4 is a sectional view along the line 4—4 of FIG. 2; and

FIG. 5 is a sectional view along the line 5—5 of FIG. 2.

DESCRIPTION OF THE PREFERRED EMBODIMENTS

Figure 1:
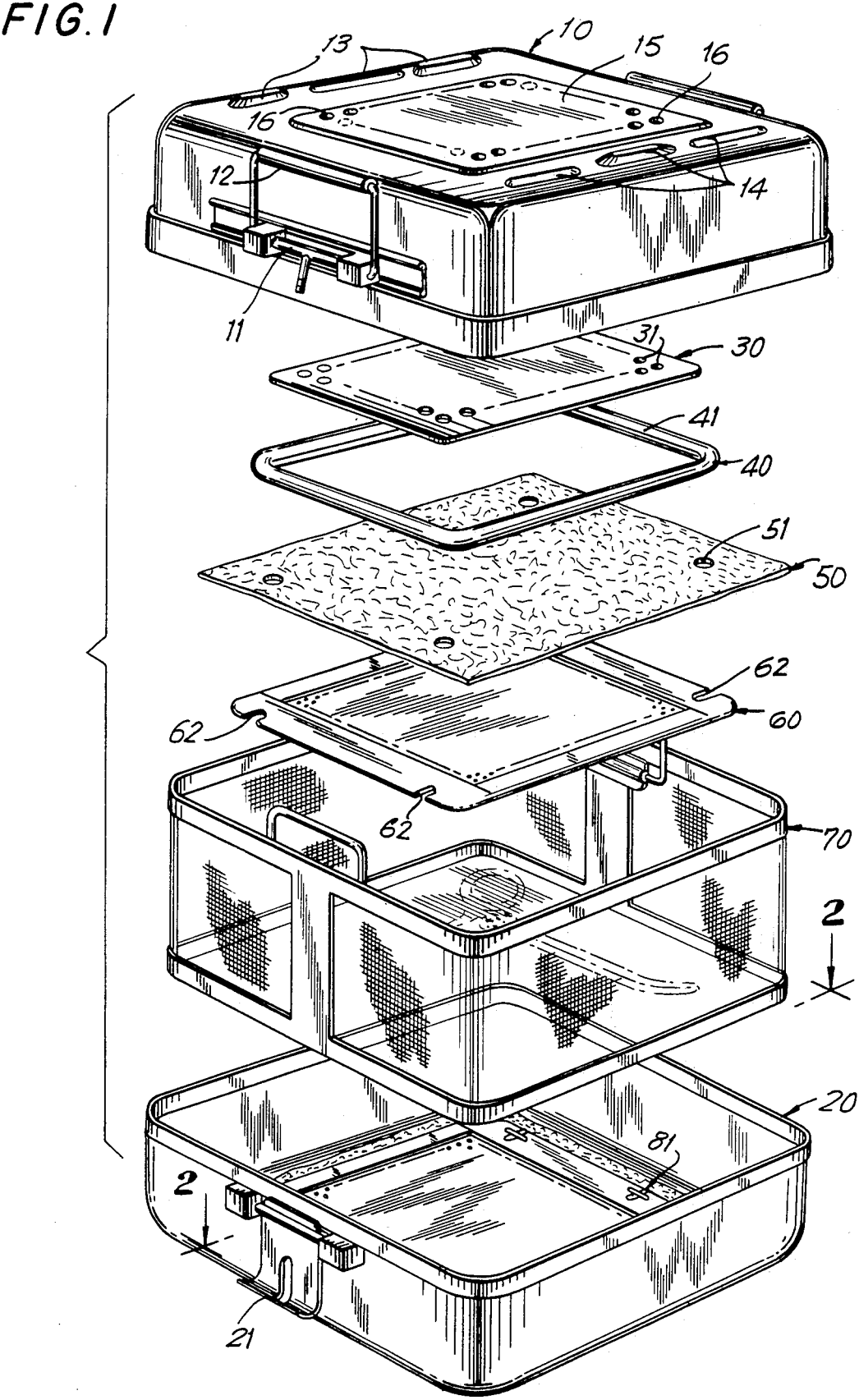
FIG. 1 is an exploded perspective view of a sterilization container including the improvement in accordance with the present invention.

Referring to the accompanying drawings, and particularly FIG. 1, 10 is the upper portion of a sterilization container and 20 is the lower portion of that container. Means for joining these two halves, 10 and 20, together to form an enclosed sterilization container are well known in the art and include the use of hasp 21 and member 11 formed, respectively, on sterilization container portions 10 and 20.

Fitted within the upper portion 10 of the sterilization container are a perforated sheet 30, a gasket 40, a filter element 50, a retaining member 60 for the filter element 50, and, as illustrated in FIG. 1, a basket 70 for retaining instruments to be sterilized. Since the basket 70 is merely exemplary of a means for holding instruments to be sterilized within the sterilization container, the basket will not be further described, but various means to accomplish this function are well known in the art.

In addition to a handle member 12 and means 11 for joining the upper portion 10 to the lower portion 20 of the sterilization container, and raised and recessed portions 13 and 14, which allow for stacking of a plurality of sterilization containers, a surface 15 is provided on the upper half of the sterilization container. This surface 15 is provided with a plurality of perforations 16 formed directly in the surface. It is through these perforations which are, generally, from ¼ to ½ inch in diameter, that damage to the instruments held within the container and loss of sterilization can be effected, absent the improvement of the present invention. The particular size and shape of the perforations 16 is not critical. Generally, the perforations are formed in regular rows, both laterally and longitudinally, and occupy approximately 20% of the overall surface of the sterilization container. However, these descriptions are not meant to be restrictions on the arrangement or size of the perforations. Generally, the outer surface of the lower portion 20 of the sterilization container is provided with similar perforations and means for stacking of a plurality of sterilization containers.

In order to preclude entry of sharp objects into the interior of the sterilization container, a perforate member 30 is held against the inside surface of the sterilization container portions 10 and 20. The size and shape of the perforations 31 on this perforate sheet are generally the same as the perforations 16 in the surface 15 of the sterilization container. The total area of perforations is also approximately the same as the area of perforations 16.

Figure 2:
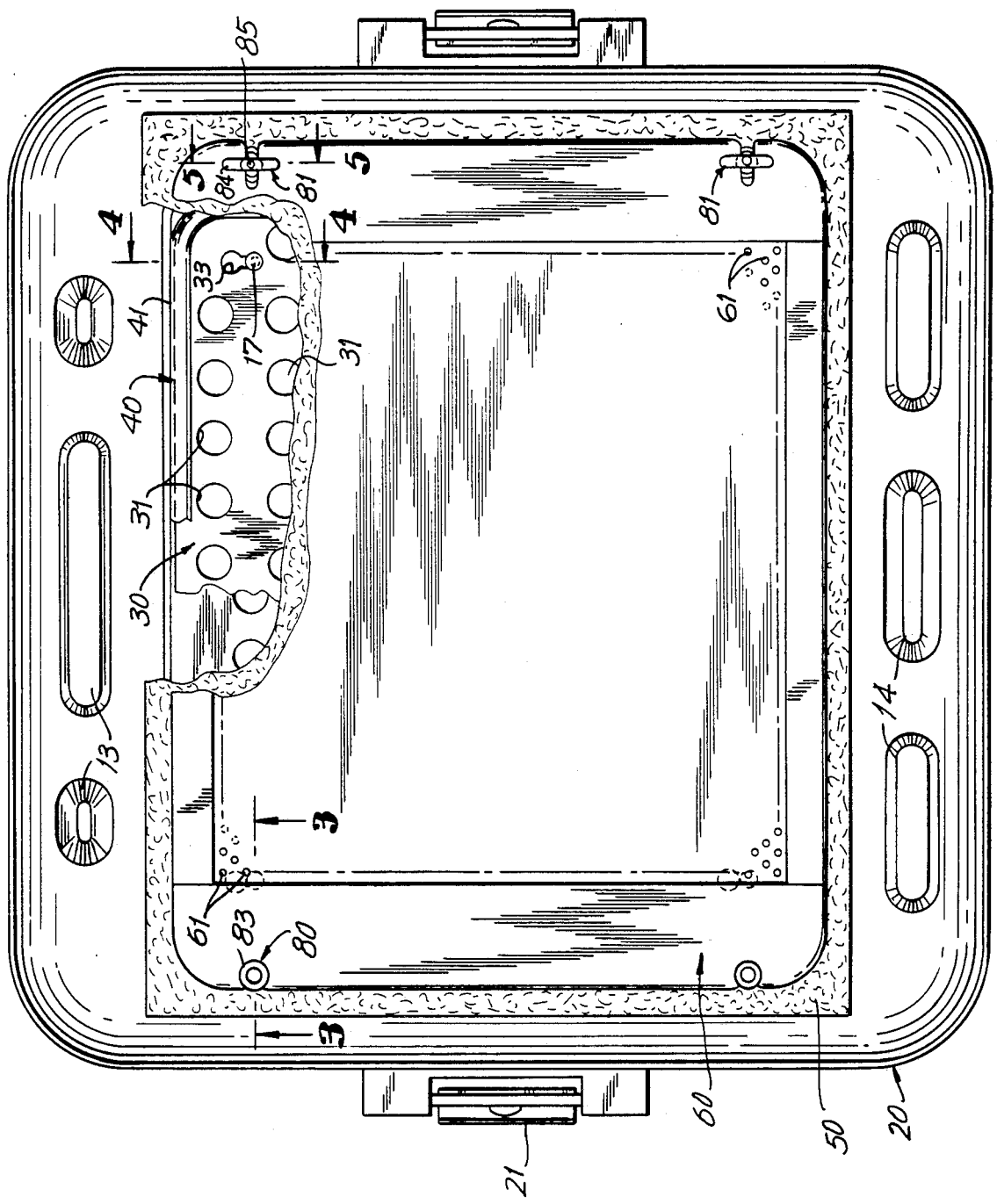
FIG. 2 is a sectional view, partially broken away, along the line 2—2 of FIG. 1.

As best illustrated in FIG. 2, the perforate sheet 30 is placed over the inner perforate surface of the sterilization container portions, and the perforations 31 are offset from the perforations 16 so that no sharp object approaching the sterilization container from the outside can penetrate both an opening 16 and an opening 31. Because of the proximity of the perforate sheet 30 to this inner portion of surface 15, even at a sharp, acute angle, penetration is not possible.

The perforate sheet 30 is held to the inner surface of the sterilization container 10 or 20 through use of headed members 17 formed on the portion 10 or 20 and keyhole slots 33 formed in the perforate member. Preferably, a keyhole slot 33 is formed near each corner of the perforate member 30 and a corresponding headed member 17 is provided for each such keyhole slot. By proper placement of the headed member 17 and keyhole slots 33, the perforate members can be placed over the headed members 17, through the larger portion of keyhole slot 33, and when the perforate sheet is then slid in a direction such that the headed member 17 occupies the smaller portion of keyhole slot 33, the perforate member is locked in a position as illustrated in FIG. 2 where the openings 31 are offset from the openings 16. The perforate sheet is a relatively stiff member, preferably formed of metal, most preferably, stainless steel.

The gasket member 40 can be formed of any of the materials which are well known for use in constructions of this type. For example, it can be formed of a silicone rubber. While it is possible to place the gasket 40 over the perforate member 30, it is preferable that the gasket member 40 be formed with a channel 41 into which the perforate sheet 30 is fitted. In this way, the gasket member 40 can act to both seal the space between the perforate member 30 and the inside of surface 15, while also acting to seal the perforate member 30 against the filter element 50. Use of a gasket member of this type, which is compressed when the headed members 17 are forced into the smaller portions of keyhole slots 33, maintains purchase between the perforate member 30 and the surface of portions 10 or 20 of the steriization container. This aids in preventing micro-organisms from migrating around the perforate sheet 30 and bypassing the filter element 50. When employed with the channel 41, the opposite side of gasket member 40 maintains purchase between the perforate sheet 30 and the filter element 50 so as to prevent migration of micro-organisms around the filter element.

Headed members 80 and pivotal retaining means 81 are provided on the inner surface of both the upper portion 10 of the sterilization container and the lower portion 20 of the sterilization container. These headed members 80 and pivotal retaining means 81 are employed to hold in place the filter element 50 and the retaining member 60.

The filter element 50, as illustrated in FIG. 1, is provided with openings or holes 51 which are spaced so as to fit over the headed members 80 and pivotal retaining means 81. Since the headed members 80 and pivotal retaining means 81 are placed outside the effective filtration area, these openings in the filter 50 do not provide a path for micro-organisms to enter the sterilized inner portion of the sterilization container or to affect the instruments which are being sterilized. The filter element 50 is generally a bacterial filter and can be any of the types generally employed in this art.

Holding the filter element 50 in place is a retaining member 60. As representationally illustrated, the retaining member 60 is provided with a plurality of openings 61 to allow for the passage of sterilant, high temperature steam or ethylene oxide gas, for example. Generally, the perforations 61 in the retaining member 60 are much smaller than the perforations 16 or 31, but generally occupy about the same portion, on a percentage basis, of the retaining member 60 as the perforations 16 and 30 do in their respective surfaces.

As best illustrated in FIGS. 1 and 2, four slots 62 are provided in the ends of the retaining member 60. To apply the retaining member of the structure, slots 62 on one end of the retaining member 60 are forced over the narrow portions 82 of the headed members 80, being retained below the head 83. The length of the portion 82 of headed member 80 is such that placing the retaining member 60 in this position causes compression of gasket member 40 to provide the advantages previously described. The slots 62 on the opposite end of retaining member 60 are then forced over the head 84 of pivotal retaining means 81, the head 81 being rotated 90° from the position illustrated in FIGS. 2 and 5, so that the retaining member 60 lies adjacent the narrow portion 85 of pivotal retaining means 81. The head 84 of pivotal retaining means 81 is then twisted 90° to the position shown in FIGS. 2 and 5 to hold the retaining member 60 in place. Again, the narrow portion 85 of pivotal retaining means 81 has a length such that the gasket 40 is placed in compression when the pivotal rtaining means head 84 is turned to its holding position.

The operation just described for assembly of the perforate sheets, filters, and retaining members are carried out on both the upper portion 10 and lower portion 20 of the sterilization container. The basket 70 or other instrument holding means is then placed within the lower portion 20 of the sterilization container, the top portion 10 of the sterilization container is then firmly attached, and the sterilization container may now be carried through a chamber where a sterilant is introduced, such as high temperature steam or ethylene oxide gas. The sterilant is free to pass through the openings 16 and 31, the filter element 50, and the perforations 61 to contact the instruments held within the tray 70 or other instrument holding device. When sterilization is completed, the sterilization container is removed from the chamber and carried to an appropriate storage area. Because the perforate sheet 30 is positioned so that the perforations 31 are offset from the perforations 16, sharp instruments are precluded from passing through the opening 16 in such a manner as to puncture the filter element 50, rendering the sterilization container nonsterile, or from damaging the instruments held within the member 70.

After the sterilization container has been opened in an operating room, and the instruments used, the assemblies connected to each of the portions 10 and 20 of the sterilization container can be disassembled and cleaned. The assemblies can then be reassembled, with a new filter element 50, and the sterilization process repeated.

Thus, in accordance with the present invention, a means has been shown to protect the integrity of a sterilization container, preventing loss of sterility or damage to the instruments held within the container. The invention should not be considered as limited to the specific examples shown and described, but only as set forth in the appended claims.

I claim:

1. In a sterilization container having a top portion and a bottom portion, said top portion having a horizontal top surface and depending vertical side surfaces, said bottom portion having vertical side surfaces and a horizontal bottom surface, wherein the vertical side surfaces of said top portion fit on top of the vertical side surfaces of the bottom portion to form a container, each portion having a perforate surface, the improvement which comprises stiff metal perforate plate means for preventing penetration of an outside object into the sterilization container, with said perforate plate means having perforations of approximately the same size and area as the perforations in the perforate surface of the sterilization container, said perforate plate means being attached parallel to the inner surface of said sterilization container having the perforate surface, the perforations in said perforate plate means being offset from the perforations in the perforate surface of said sterilization container during all phases of use of said sterilization container.

2. The sterilization container of claim 1 wherein gaskets are provided between said perforate plate means and said inner surfaces of said sterilization container.

3. The sterilization container of claim 1 wherein the perforate plate means is attached to the inner surface of said sterilization container employing headed posts on the inner surface of said sterilization container and aligned keyhole slots on said perforate plate means.

4. The sterilization container of claim 1 having, in addition, a filter element and a retaining member for said filter element, said filter element being adjacent said plate means perforate and said retaining member being on the side of said filter element opposite said perforate plate means.

5. The sterilization container of claim 4 wherein retention means are formed on the inner surface of said sterilization container to provide for retention of said retaining member, said retention means including headed posts, the heads of said headed posts beign spaced from said inner surface, said retaining member being held between said inner surface and the heads of said headed posts.

6. The sterilization container of claim 5 wherein said headed posts are employed for holding one end of said retaining member, the opposite end of said retaining member being held by pivotal retaining means.

* * * * *